United States Patent [19]

Taverna et al.

[11] Patent Number: 5,617,858
[45] Date of Patent: Apr. 8, 1997

[54] APPARATUS FOR ENDOSCOPIC OR GASTROSCOPIC EXAMINATION

[75] Inventors: Giuseppe Taverna, Zürich; Michel Boehrer, Uster; Rolf Jenni, Zürich, all of Switzerland

[73] Assignee: Vingmed Sound A/S, Horten, Norway

[21] Appl. No.: 503,750

[22] Filed: Jul. 28, 1995

[30] Foreign Application Priority Data

Aug. 30, 1994 [NO] Norway .................................. 943213

[51] Int. Cl.$^6$ ............................. A61B 5/05; A61B 8/12; A61B 1/005
[52] U.S. Cl. ............................... 128/653.1; 128/662.06; 600/109
[58] Field of Search ........................... 128/660.08–660.1, 128/660.04, 662.03–662.06; 600/101, 109; 348/65, 73, 77

[56] References Cited

U.S. PATENT DOCUMENTS

| | | | |
|---|---|---|---|
| 4,062,237 | 12/1977 | Fox | 28/660.05 X |
| 4,802,487 | 2/1989 | Martin et al. | 600/109 X |
| 4,898,175 | 2/1990 | Noguchi | 600/109 X |
| 5,005,559 | 4/1991 | Blanco et al. | 600/117 X |
| 5,211,167 | 5/1993 | Amenomori | 128/660.04 |
| 5,239,982 | 8/1993 | Trauthen | 600/117 |
| 5,297,346 | 3/1994 | Weiner | 33/512 |
| 5,347,987 | 9/1994 | Feldstein et al. | 600/109 |
| 5,400,771 | 3/1995 | Pirak et al. | 600/109 |
| 5,469,254 | 11/1995 | Konomura | 600/109 |
| 5,475,613 | 12/1995 | Itoga et al. | 128/660.07 X |

FOREIGN PATENT DOCUMENTS

| | | | |
|---|---|---|---|
| 0501819 | 2/1992 | European Pat. Off. | A61B 8/12 |
| 60-217326 | 10/1985 | Japan | G02B 23/21 |
| 3295534 | 12/1991 | Japan | 600/117 |
| 2073418 | 10/1981 | United Kingdom | A61B 10/00 |
| 2074733 | 11/1981 | United Kingdom | A61B 10/00 |
| 9320876 | 10/1993 | WIPO | A61M 25/01 |

Primary Examiner—Francis Jaworski
Attorney, Agent, or Firm—Rothwell, Figg, Ernst & Kurz, P.C.

[57] ABSTRACT

Apparatus for endoscopic or gastroscopic examination of patients, comprising an endoscope (5) having a probe head (6) provided with an imaging transducer being preferably an ultrasonic or camera-based transducer, said endoscope (5) being adapted to be inserted through the mouth of the patient, and position detection means (7,15) to provide probe head position information which together with corresponding imaging examination results are adapted to be stored in recording means (24). As known per se the endoscope (5) has a visible distance scale or indication (15) along a length thereof. The position detection means comprise a small video camera (7) with a mounting device (7A) for holding the camera in a fixed position in relation to the patient's teeth and with the field of view of the camera covering said endoscope (5) and said distance scale or indication (15) thereon, at the point of entering the patient's mouth.

7 Claims, 1 Drawing Sheet

APPARATUS FOR ENDOSCOPIC OR GASTROSCOPIC EXAMINATION

BACKGROUND OF THE INVENTION

This invention relates to an apparatus for the endoscopic or gastroscopic examination of patients, comprising an endoscope having a probe head provided with an imaging transducer being preferably an ultrasonic or camera-based transducer, whereby the endoscope according to common practice is adapted to be inserted through the mouth of the patient.

It is an advantage of the present invention that such an apparatus comprises position detection means to provide probe head position information which together with corresponding imaging examination results are adapted to be stored in recording means.

Thus, in connection with many examinations of the kind contemplated here, there is a need for determining and recording the position of the probe or ultrasonic head during the examination procedure concerned. This in particular is of interest when examination results obtained at different times or different locations shall be compared in order to follow the development of some defect or disease. For example, recording means being useful for this purpose may be based on storage media such as video tapes or the like.

Prior art being more or less of interest in connection with apparatus for examination of the kind contemplated here, can be summarized briefly as follows.

GB 2,073,418 describes an ultrasonic probe for examining a gastrointestinal tract and adjacent organs, whereby the output of a position recorder may be recorded together with an image produced by the probe, to provide an indication of the location of the probe corresponding to the image.

U.S. Pat. No. 5,295,486 relates to transesophageal echocardiography whereby a probe position is detected by means of induction coils and loops being in part integrated into the patient's gurney. This manner of position detection will tend to be inaccurate and the whole system described is rather complicated.

GB 2,074,733 shows ultrasonic diagnostic apparatus whereby the position of an ultrasonic probe is detected and stored in a memory, and on a display screen the position of the ultrasonic probe and an ultrasonic tomogram are shown simultaneously. This known apparatus, however, is not intended for endoscopic or gastroscopic examination.

U.S. Pat. No. 4,896,673 describes a system for localizing for example a gallstone in a human patient whereby the position of an ultrasonic transducer is monitored by means of cameras. As in the British patent specification referred to immediately above this known system is not related to endoscopic or gastroscopic examination.

EP 0,501,819 relates to ultrasonic diagnostic apparatus comprising an ultrasonic probe to be inserted into a body cavity of a patient under examination. Means are provided for manually introducing indications of the posture held by the patient during ultrasonic imaging in order to facilitate an accurate diagnosis.

U.S. Pat. No. 5,156,155 shows in its FIG. 1 that an endoscope having a visible distance scale or indication along a length thereof, is known per se.

U.S. Pat. No. 4,642,687 describes an apparatus for producing or combining superimposed images from two different sources or systems, such as a video camera. This known apparatus, however, is not described in connection with ultrasonic head position information which together with corresponding imaging examination results are to be stored in suitable recording means or devices.

SUMMARY OF THE INVENTION

In view of what is previously known, a primary object of the present invention is to provide a simplified and yet accurate apparatus of the kind stated in the introductory paragraphs above, while at the same time offering practical advantages during actual use of the apparatus.

Thus, the novel and specific features of the apparatus according to this invention in the first place consists therein that the endoscope as known per se has a visible distance scale or indication along a length thereof, that the position detection means comprise a small video camera with a mounting device for holding the camera in a fixed position in relation to the patients teeth and with the field of view of the camera covering the endoscope and the distance scale or indication thereon, at the point of entering the patients mouth.

Among the advantages obtained it is to be noted that the present apparatus to a high degree is based upon at one hand usual or well known components, such as the video camera, and on the other hand quite simple although specific components such as the mounting device for holding the camera, whereby such device preferably comprises a biteguard (mouthpiece) adapted to be clamped between the patient's teeth during the examination.

Due to the simple and reliable operating principles involved, practitioners in hospitals and other medical centers will not need much training or instruction to be able to operate this apparatus. Taking the row or rows of teeth of the patient as a reference, the position determination and recordation will be very well defined, for example by having a centimeter scale as the visible distance scale or indication along the length of the endoscope, as mentioned above. In actual practice therefore, repeated examinations of the same area, such as the heart with the aorta, will be reproducible. This means that disease survey by employing this apparatus will be more representative and reliable.

DETAILED DESCRIPTION OF THE PREFERRED EMBODIMENTS

Figure 1:
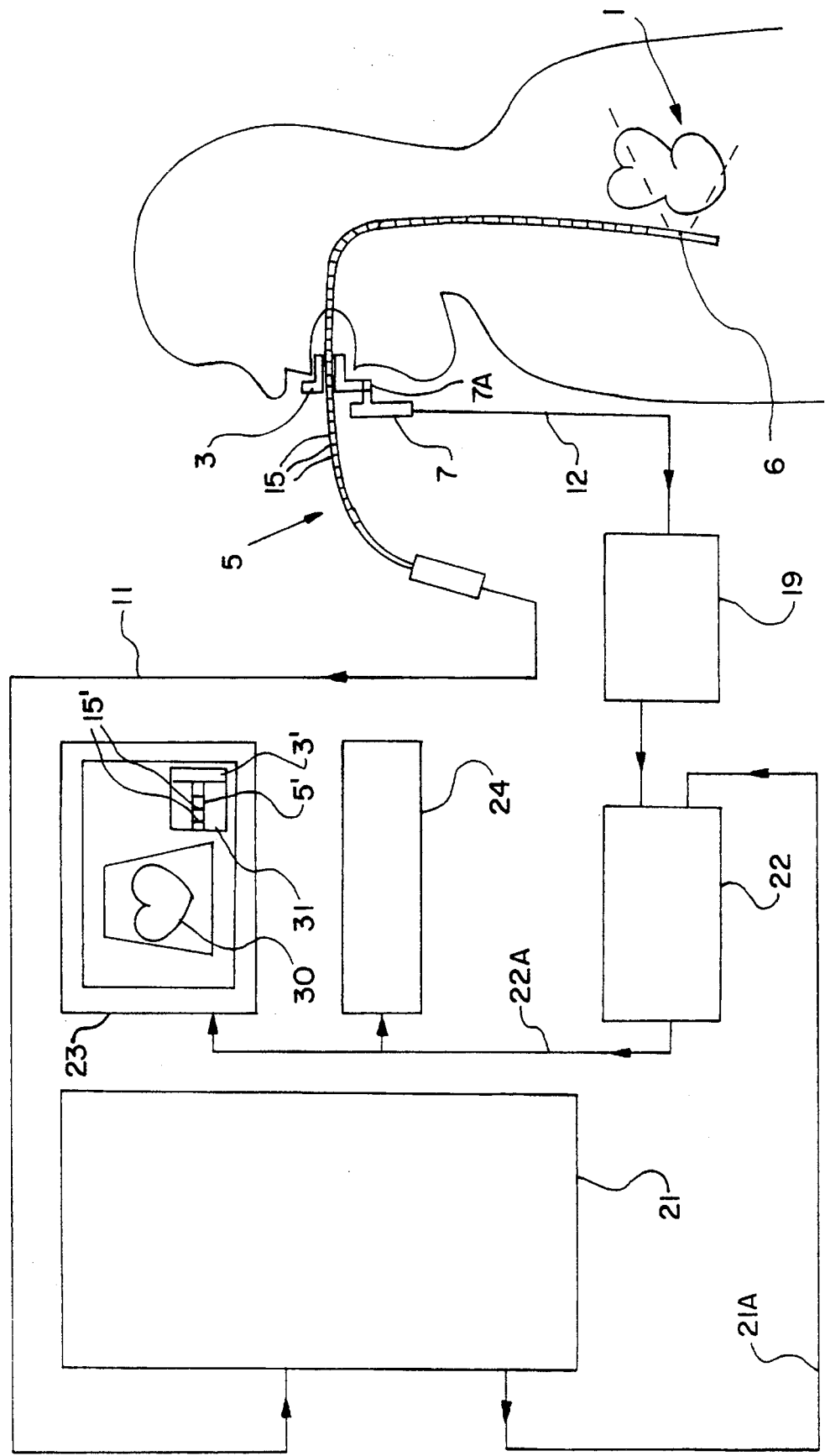
FIG. 1 is a schematic diagram of an apparatus according to a preferred embodiment of the invention.

An embodiment of the apparatus according to this invention will be explained more closely below with reference to the drawing, which in a schematic and simplified manner shows the apparatus in use with a patient the heart region of which is to be examined.

To the right in the drawing a patient is shown, including the heart 1 which is subjected to endoscopic examination, by means of a probe head 6 at the tip of an endoscope 5. The probe or transducer head may for example be adapted for mapping regions of the heart 1, such as the aorta.

Although this invention has been developed primarily in connection with ultrasonic methods as just mentioned, other uses may be contemplated, for example in gastroscopic methods and with a probe head carrying a camera or other optical sensor means.

As shown, the endoscope 5 is inserted through the mouth of the patient according to common practice, and as known per se the endoscope 5 is provided with indications 15 constituting a distance or length scale which may for example be in centimeters with the distal tip at the end of probe 6 taken as the origin or zero reference point. Accordingly, in the complete position detection arrangement to be described below, there is no need for calibration as to the length of the endoscope having been inserted through the patient's mouth, and the examination is individually reproducible with respect to each patient without calibration.

An important component in the apparatus according to the invention is in the form of a mouthpiece or a biteguard 3 to be held between the patient's teeth so as to have a very well defined and fixed position during examination. As will be seen in the drawing mouthpiece 3 has an outer somewhat flange like part and a more narrow part projecting from the flange part between the teeth into the mouth of the patient. This projecting part is dimensioned and shaped so as to be securely located between the patient's teeth and at the same time to be comfortable to the patient. Suitable plastic materials are available for the parts of this mouthpiece 3.

Centrally through mouthpiece 3 there is a through opening for the endoscope 5 to be introduced as illustrated in the drawing. A small bracket or support 7A attached to the mouthpiece 3 is adapted to hold a miniature video camera 7 in a position to be able to read or detect the distance scale or indications 15 on the endoscope 5 at the point of entering mouthpiece 3. Thus, the outwardly facing front surface of mouthpiece 3 can be taken as a reference plane or point in relation to which the distance markings are observed by means of camera 7. This constitutes a very straightforward and reliable principle of position determination and recording of the actual position of probe head 6 in the zone of interest at any time during an examination. It is essential in this connection to have such probe head position information stored or recorded together with and simultaneously with imaging information resulting from the examination by means of probe head 6.

For the necessary control operations, signal processing and recording with respect to the two information contributions just mentioned above, there is shown in block schematic form in the drawing, an ultrasonic unit 21 which in the principle can be of commonly known types in ultrasonic medical acquisition and examination systems, to which imaging information is conveyed through a cable 11 which also contains conductors for various control functions in connection with endoscope 5 and in particular the probe head 6. As shown, there is provided an endoscope control device 5A containing mechanical and electrical elements for the manipulation and operation of endoscope 5 as a whole. From camera 7 a cable 12 is provided to convey position information via a camera control unit 19 into a combining or processing unit 22. This unit also receives imaging information or video signals 21A from ultrasonic unit 21 in order to combine the imaging and the position information for display or recording, such combining (picture-in-picture) being known per se, for example according to the principles described in U.S. Pat. No. 4,642,687 referred to above.

An output 22A is shown from combining unit 22 leading to a display unit 23 on the screen of which exemplary illustrations of interest during examination of a patient is shown. This comprises an ultrasonic section 30 of the heart region of interest, showing for example various blood flow velocities within the heart structures or regions which may have defects. On the same screen and simultaneously with presentation 30 there is a window 31 showing the picture or scene imaged by camera 7. Thus, more particularly window 31 shows a portion of the mouthpiece 3', a portion 5' of the endoscope with distance indications 15' thus presenting to the examining personel both the ultrasonic picture or section information and the accurate position information as to where the probe head is positioned within the patient and in relation to the heart 1. Tests have shown that the patient's teeth constitute a very reliable position reference in this apparatus or system. Of course the scale or indications 15 or 15' are accompanied by a centimeter scale which can also be read in window 31 on display screen 23, although for clarity such centimeter scale or numbers are not shown in the drawing.

In addition to display screen or unit 23, and perhaps more important, there is provided a recording unit 24 being also connected to combining unit through line 22A, thus being adapted to receive the combined signal or information corresponding to what is displayed in unit 23. Thus, when recording such information for example on a video tape, the examination results together with position information as explained, can be stored for later use so that the results of one examination may be compared with results of corresponding examinations at an earlier or a later time.

We claim:

1. An apparatus for endoscopic or gastroscopic examination of patients, comprising:

an endoscope having a probe head provided with an imaging transducer, said endoscope being adapted to be inserted through the mouth of a patient, position detection means for providing probe head position information, said endoscope having a visible distance scale along a length thereof, said position detection means including a small video camera with a mounting device for holding the camera in a fixed position in relation to the patient's teeth and with the field of view of the camera covering said endoscope and said distance scale thereon, at the point of entering the patient's mouth.

2. The apparatus according to claim 1, wherein said mounting device includes a mouthpiece adapted to be clamped between the patient's teeth and provided with a through opening for inserting said endoscope.

3. The apparatus according to claim 2, wherein an axis of the field of view of said camera is oriented generally perpendicular an axis of said through opening.

4. The apparatus of claim 3, wherein said axis of said field of view of said camera intersects said axis of said through opening.

5. The apparatus of claim 1, wherein said imaging transducer is an ultrasonic transducer.

6. The apparatus of claim 1, wherein said imaging transducer is a camera-based transducer.

7. The apparatus of claim 1, further including a recorder for storing said probe head information and corresponding imaging examination results from said imaging transducer.

* * * * *